US006406722B1

(12) United States Patent
Gallaher

(10) Patent No.: US 6,406,722 B1
(45) Date of Patent: Jun. 18, 2002

(54) METHOD OF TREATING VIRAL INFECTIONS AND LESIONS WITH TAXANE COMPOUNDS

(76) Inventor: Robert G. Gallaher, 12339 20$^{th}$ Ave. NE., Seattle, WA (US) 98125

( * ) Notice: Subject to any disclaimer, the term of this patent is extended or adjusted under 35 U.S.C. 154(b) by 0 days.

(21) Appl. No.: 09/506,415

(22) Filed: Feb. 17, 2000

Related U.S. Application Data

(60) Provisional application No. 60/120,582, filed on Feb. 18, 1999.

(51) Int. Cl.$^7$ .......................... A01N 65/00; A61K 35/78

(52) U.S. Cl. ....................................... 424/775; 424/725

(58) Field of Search ................................ 514/449, 549; 549/510, 195.1; 424/725, 775

(56) References Cited

U.S. PATENT DOCUMENTS

| | | | | |
|---|---|---|---|---|
| 5,478,736 A | * | 12/1995 | Nair ............................ | 435/123 |
| 5,800,817 A | * | 9/1998 | Verge et al. ............... | 424/195.1 |
| 6,057,359 A | | 6/2000 | Eugster ....................... | 514/449 |
| 6,177,469 B1 | | 1/2001 | Zilch et al. .................. | 514/558 |

OTHER PUBLICATIONS

Norrild, B., Velli–Pekka, L., Vertanen, I., Organization of Cytoskeleton Elements during Herpes Simplex Virus Type 1 Infection of Human Fibroblast: An Immunofluorescence Study. J. gen. Virol. (1986), 67, 97–105.

Kristensson, K., Lycke, E., et al, Neuritic Transport of Herpes Simplex Virus in Rat Sensory Neurons in vitro. Effects of Substances Interacting with Microtubular Function and Axonal Flow [Nocodazole, Taxol and Erkytho–9–3(2–hydroxkynonyl)adenine]. J. gen. Virol. (1986), 67, 2023–2028.

Sodeik, B., Ebersold, M., Helenius, A., Microtubule–mediated Transport of Incoming Herpes Simplex Virus 1 Capsids to the Nucleus. The Journal of Cell Biology (Mar. 10, 1997), vol. 136, No. 5, 1007–1021.

* cited by examiner

Primary Examiner—Jon P. Weber
Assistant Examiner—Patricia D Patten
(74) Attorney, Agent, or Firm—Black Lowe & Graham PLLC

(57) ABSTRACT

The present invention provides compositions and methods for treating diseased, biological tissue; such as the epidermis or mucous membranes, in a mammal. Compositions of the present invention can be used to treat epidermal lesions, such as those resulting from viral and bacterial infections. In one embodiment, the present invention provides compositions useful for treating diseased, biological tissue, such as the epidermis or mucous membranes, in a mammal. The compositions of the present invention include at least one taxane. Preferably, the compositions of the present invention also include a natural oil, such as olive oil, and a wax, such as bees wax. In another embodiment, the present invention includes a method of treating diseased biological tissue, such as the epidermis or mucous membranes, in a mammal. The method of the present invention includes the step of contacting a diseased biological tissue, such as the epidermis, with a composition of the present invention containing an amount of a taxane, taxoid, or related compound, that is effective to ameliorate the disease symptoms.

8 Claims, 11 Drawing Sheets

FIGURE 1A. Drug Screening Report for TBT, Lot ARB-ID#99-332

| VEHICLE | 634 μg /ml in EtOH | | | UNIT mg |
|---|---|---|---|---|
| LOT #1 | | TRIAL #1 | | |
| HSV-1 (HFF Cells) | | | | |
| CPE Inhibition – MCG/ML | | | | |
| 09/17/98 | EC50 >10 | CC50 >10 | SI = 0 | ACV EC50 = 1.2 |
| Plaque Reduction – MCG/ML | | | | |
| 10/19/98 | EC50 = 5.9 | CC50 >10 | SI >1.6 | ACV EC50 = 0.3 |
| HSV-2 (HFF Cells) | | | | |
| CPE Inhibition – MCG/ML | | | | |
| 09/17/98 | EC50 = 2.0 | CC50 >10 | SI >6.0 | ACV EC50 = 1.9 |
| Plaque Reduction – MCG/ML | | | | |
| 10/19/98 | EC50 = 0.9 | CC50 >10 | SI >11.1 | ACV EC50 = 0.1 |
| HCMV (HFF Cells) | | | | |
| CPE Inhibition – MCG/ML | | | | |
| 10/01/98 | EC50 = 5.0 | CC50 >10 | SI >2.0 | GCV EC50 = 0.06 |
| Plaque Reduction – MCG/ML | | | | |
| / / | EC50 | CC50 | SI | GCV EC50 |
| MCMV (HFF Cells) | | | | |
| Plaque Reduction – MCG/ML | | | | |
| / / | EC50 | CC50 | SI | CCV EC50 |
| VZV (HFF Cells) | | | | |
| CPE Inhibition – MCG/ML | | | | |
| / / | EC50 | CC50 | SI | ACV EC50 |
| | | | | |
| Plaque Reduction – MCG/ML | | | | |
| / / | EC50 | CC50 | SI | CCV EC50 |

Cytopathic Effect Inhibition and Plaque Reduction Assays For HSV-1, HSV-2, HCMV, MCMV, and VSV, in HFF cell cultures.

FIGURE 1B. Drug Screening Report for TBT, Lot ARB-ID#99-332

| EBV | | | | |
|---|---|---|---|---|
| VCA – MCG/ML (In Daudi Cells) | | | | |
| 10/16/98 | EC50 = 1.4 | CC50 = 0.21 | SI = 0 | ACV EC50 = 1.8 |
| EBV DNA – MCG/ML (In Daudi Cells) | | | | |
| / / | EC50 | CC50 | SI | ACV EC50 |
| Toxicity Assays | | | | |
| Neutral Red Uptake – MCG/ML (In Stationary HFF Cells) | | | | |
| 09/17/98 | CC50 >10 | ACV IC50 >100 | | GCV IC50 >100 |
| Cell Proliferation – MCG/ML (In Rapidly Growing Daudi Cells) | | | | |
| 10/16/98 | IC50 <0.08 | | ACV IC50 >50 | |
| Cell Proliferation – MCG/ML (In Rapidly Growing HFF Cells) | | | | |
| 10/16/98 | IC50 0.02 | ACV IC50 >100 | | GCV IC50 40.0 |
| Comments and Recommendations: HCMV PR. This compound is problematic. | | | | |

Cytopathic Effect Inhibition and Plaque Reduction Assays EBV in DAUDI cell cultures; Toxicity Assays in HFF and DAUDI cell cultures.

FIGURE 2. HSV ELISA METHOD

1. Remove the growth media HFF cells.
2. Add 100 μl of MEM to the 6 cell control wells.
3. Add 50 μl of the diluted virus to the remaining wells.

A. Herpes simplex virus type 1, ATCC # V-733, strain F. HSV-1 (5/3/96), one plate. Dilute stock 1:2000, 2.0 μl in 4.0 ml MEM.

B. Herpes simplex virus type 2, ATCC # VR-734, strain G. HSV-2 (5/3/96), one plate. Dilute stock 1:2000, 2.0 μl + 4.0 ml MEM.

Clinical strains.

1. Specimen # 1. HSV-1, December 9, 1997, eye. Dilute stock 1:500, 8.0 μl plus 4.0 ml of MEM.
   2. Specimen # 2, HSV-1, September 30, 1997, oral pharynx. Dilute stock 1:50, 60 μl plus 3.0 ml of MEM.
   3. Specimen # 3, HSV-2, Nov. 26, 96, oral pharynx. Dilute stock 1:500, 8.0 μl plus 4.0 ml of MEM.
   4. Specimen # 4, HSV-2, Dec. 27, 96, ETT. Dilute stock (May 27, 98) 1:100, 40.0 μl plus 4.0 ml of MEM.
   5. Specimen # 5. HSV-2, April 11, 1998, penis. Dilute stock 1:100, 40 μl plus 4.0 ml of MEM.
   6. Specimen # 6. HSV-2, April 24, 1998. Dilute stock 1:100, 40 μl plus 4.0 ml of MEM.

4. Add the virus to the plates for one hour and incubate the plates at 37° C.
5. Remove the virus inoculum and add 100 μl of MEM to the virus control wells and add 100 μl of diluted drug to each of the remaining wells.

TBT. Stock TBT contains 624 μg/ml of active component, 10-deacetyl-7-xylosyltaxol in 50% ethanol from Rainbow Botanics.

a. Warm the TBT and 1X MEM to 37° C. The stock TBT was diluted to 4.0 μg/ml by adding 154 μl of TBT to 24,000 μl of 1X MEM.

| TBT, μg/ml | 4.0 | 3.0 | 2.0 | 1.0 | 0.75 | 0.5 | 0.25 | 0.1 |
|---|---|---|---|---|---|---|---|---|
| Vol. Of extract, μl. | 6000 | 6000 | 4000 | 2000 | 1500 | 1000 | 500 | 200 |
| MEM, μl. | - | 2000 | 4000 | 6000 | 6500 | 7000 | 7500 | 7800 |

ELISA RESULTS:

Antibody to HSV-1 was used at a 1:2000 dilution. Antibody to HSV-2 was used at a 1:1500 dilution. Read with dual wavelength, 630 – 490 nm.

FIGURE 3
HSV-1 ELISA CONTROL (ATCC VR-733, STRAIN F)

| CC | VC | 4 | 3 | 2 | 1 | 0.75 | 0.5 | 0.25 | 0.1 | μg/ml |
|---|---|---|---|---|---|---|---|---|---|---|
| 0.000 | 0.361 | 0.069 | 0.129 | 0.188 | 0.373 | 0.360 | 0.367 | 0.309 | 0.305 | |
| 0.000 | 0.231 | 0.046 | 0.093 | 0.236 | 0.349 | 0.357 | 0.329 | 0.352 | 0.362 | |
| 0.000 | 0.304 | 0.052 | 0.114 | 0.206 | 0.358 | 0.327 | 0.291 | 0.355 | 0.354 | |
| 0.000 | 0.295 | 0.033 | 0.097 | 0.247 | 0.338 | 0.354 | 0.306 | 0.316 | 0.381 | |
| 0.000 | 0.290 | 0.039 | 0.098 | 0.241 | 0.312 | 0.301 | 0.347 | 0.346 | 0.361 | |
| 0.000 | 0.303 | 0.045 | 0.065 | 0.203 | 0.344 | 0.349 | 0.333 | 0.362 | 0.346 | |
| | | | | | | | | | | |
| 0.000 | 0.297 | 0.047 | 0.099 | 0.220 | 0.346 | 0.341 | 0.329 | 0.340 | 0.352 | |
| | | | | | | | | | | |
| | 0.297 | 0.047 | 0.099 | 0.220 | 0.346 | 0.341 | 0.329 | 0.340 | 0.352 | |
| | | | | | | | | | | |
| | | 15.9 | 33.4 | 74.0 | 116.3 | 114.8 | 110.6 | 114.3 | 118.2 | |
| DATE: 6/24/98 | | | | | INOC: 6/22/98 | | | | | |
| DRUG: TBT | | | | | VIRUS: HSV-1 | | | | | |
| | | | | | Control TBT-IC50 = 3 μg/ml | | | | | |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 μg/ml Taxus Brevifolia Tincture (TBT) has been added.

FIGURE 4
HSV-1 ELISA, CLINICAL SPECIMEN #1

| CC | VC | 4 | 3 | 2 | 1 | 0.75 | 0.5 | 0.25 | 0.1 | μg/ml |
|---|---|---|---|---|---|---|---|---|---|---|
| 0.000 | 0.387 | 0.147 | 0.155 | 0.157 | 0.331 | 0.256 | 0.319 | 0.272 | 0.368 | |
| 0.000 | 0.279 | 0.107 | 0.166 | 0.161 | 0.273 | 0.235 | 0.258 | 0.238 | 0.370 | |
| 0.002 | 0.256 | 0.109 | 0.115 | 0.203 | 0.289 | 0.187 | 0.258 | 0.245 | 0.368 | |
| 0.000 | 0.328 | 0.110 | 0.135 | 0.216 | 0.295 | 0.251 | 0.231 | 0.274 | 0.370 | |
| 0.005 | 0.328 | 0.102 | 0.142 | 0.249 | 0.327 | 0.318 | 0.294 | 0.366 | 0.314 | |
| 0.003 | 0.344 | 0.098 | 0.198 | 0.204 | 0.316 | 0.311 | 0.324 | 0.374 | 0.362 | |
| | | | | | | | | | | |
| 0.002 | 0.320 | 0.112 | 0.152 | 0.198 | 0.305 | 0.260 | 0.281 | 0.295 | 0.359 | |
| | | | | | | | | | | |
| | 0.319 | 0.111 | 0.150 | 0.197 | 0.304 | 0.258 | 0.279 | 0.293 | 0.357 | |
| | | | | | | | | | | |
| | | 34.7 | 47.1 | 61.7 | 95.2 | 81.0 | 87.6 | 92.0 | 112.0 | |

| | |
|---|---|
| DATE: 6/24/98 | INOC: 6/22/98 |
| DRUG: TBT | VIRUS: HSV-1 |
| | Specimen #1  TBT-IC50 = 3 μg/ml |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 μg/ml Taxus Brevifolia Tincture (TBT) has been added.

FIGURE 5
HSV-1 ELISA, CLINICAL SPECIMEN #2

| CC | VC | 4 | 3 | 2 | 1 | 0.75 | 0.5 | 0.25 | 0.1 | µg/ml |
|---|---|---|---|---|---|---|---|---|---|---|
| 0.005 | 0.238 | 0.016 | 0.005 | 0.020 | 0.048 | 0.061 | 0.029 | 0.029 | 0.062 | |
| 0.002 | 0.086 | 0.005 | 0.019 | 0.050 | 0.053 | 0.054 | 0.080 | 0.080 | 0.056 | |
| 0.009 | 0.111 | 0.010 | 0.000 | 0.000 | 0.033 | 0.027 | 0.104 | 0.104 | 0.077 | |
| 0.006 | 0.141 | 0.034 | 0.011 | 0.022 | 0.065 | 0.059 | 0.059 | 0.059 | 0.109 | |
| 0.012 | 0.186 | 0.002 | 0.057 | 0.110 | 0.061 | 0.087 | 0.108 | 0.108 | 0.086 | |
| 0.006 | 0.196 | 0.018 | 0.039 | 0.017 | 0.031 | 0.087 | 0.090 | 0.090 | 0.120 | |
|  |  |  |  |  |  |  |  |  |  | |
| 0.007 | 0.160 | 0.014 | 0.022 | 0.037 | 0.049 | 0.063 | 0.078 | 0.078 | 0.085 | |
|  |  |  |  |  |  |  |  |  |  | |
|  | 0.153 | 0.008 | 0.015 | 0.030 | 0.042 | 0.056 | 0.072 | 0.072 | 0.078 | |
|  |  |  |  |  |  |  |  |  |  | |
|  |  | 4.9 | 9.9 | 19.5 | 27.3 | 36.5 | 46.8 | 46.8 | 51.2 | |
| DATE: 6/24/98 | | | | | INOC: 6/22/98 | | | | | |
| DRUG: TBT | | | | | VIRUS: HSV-1 | | | | | |
| | | | | | Specimen #2 TBT-IC50 = 0.25 µg/ml | | | | | |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 µg/ml Taxus Brevifolia Tincture (TBT) has been added.

FIGURE 6
HSV-2 ELISA CONTROL (ATCC VR-734, STRAIN G)

| CC | VC | 4 | 3 | 2 | 1 | 0.75 | 0.5 | 0.25 | 0.1 | µg/ml |
|---|---|---|---|---|---|---|---|---|---|---|
| 0.007 | 0.172 | 0.019 | 0.053 | 0.033 | 0.098 | 0.065 | 0.088 | 0.179 | 0.244 | |
| 0.007 | 0.148 | 0.016 | 0.049 | 0.074 | 0.079 | 0.108 | 0.125 | 0.150 | 0.201 | |
| 0.005 | 0.147 | 0.024 | 0.014 | 0.117 | 0.066 | 0.086 | 0.079 | 0.113 | 0.245 | |
| 0.015 | 0.169 | 0.044 | 0.033 | 0.060 | 0.070 | 0.097 | 0.107 | 0.124 | 0.203 | |
| 0.029 | 0.231 | 0.026 | 0.045 | 0.073 | 0.068 | 0.080 | 0.108 | 0.155 | 0.223 | |
| 0.008 | 0.148 | 0.015 | 0.031 | 0.053 | 0.067 | 0.103 | 0.085 | 0.104 | 0.177 | |
| | | | | | | | | | | |
| 0.012 | 0.169 | 0.024 | 0.038 | 0.068 | 0.075 | 0.090 | 0.099 | 0.138 | 0.216 | |
| | | | | | | | | | | |
| | 0.157 | 0.012 | 0.026 | 0.057 | 0.063 | 0.078 | 0.087 | 0.126 | 0.204 | |
| | | | | | | | | | | |
| | | 7.7 | 16.3 | 35.9 | 39.9 | 49.6 | 55.2 | 79.9 | 129.4 | |
| DATE: 6/24/98 | | | | | INOC: 6/22/98 | | | | | |
| DRUG: TBT | | | | | VIRUS: HSV-2 | | | | | |
| | | | | | Control TBT-IC50 = 0.75 µg/ml | | | | | |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 µg/ml Taxus Brevifolia Tincture (TBT) has been added.

FIGURE 7
HSV-2 ELISA, CLINICAL SPECIMEN #3

| CC | VC | 4 | 3 | 2 | 1 | 0.75 | 0.5 | 0.25 | 0.1 | μg/ml |
|---|---|---|---|---|---|---|---|---|---|---|
| 0.015 | 0.337 | 0.119 | 0.109 | 0.145 | 0.290 | 0.137 | 0.200 | 0.264 | 0.204 | |
| 0.008 | 0.266 | 0.109 | 0.105 | 0.168 | 0.167 | 0.129 | 0.124 | 0.249 | 0.248 | |
| 0.010 | 0.207 | 0.056 | 0.077 | 0.154 | 0.215 | 0.106 | 0.158 | 0.191 | 0.253 | |
| 0.015 | 0.213 | 0.079 | 0.134 | 0.141 | 0.171 | 0.155 | 0.288 | 0.183 | 0.165 | |
| 0.027 | 0.211 | 0.131 | 0.090 | 0.105 | 0.171 | 0.122 | 0.203 | .0189 | 0.168 | |
| 0.007 | 0.217 | 0.070 | 0.080 | 0.059 | 0.139 | 0.132 | 0.110 | 0.125 | 0.145 | |
| | | | | | | | | | | |
| 0.014 | 0.242 | 0.094 | 0.099 | 0.129 | 0.192 | 0.130 | 0.181 | 0.200 | 0.197 | |
| | | | | | | | | | | |
| | 0.228 | 0.080 | 0.086 | 0.115 | 0.179 | 0.117 | 0.167 | 0.187 | 0.184 | |
| | | | | | | | | | | |
| | | 35.2 | 37.5 | 50.4 | 78.2 | 51.1 | 73.1 | 81.7 | 80.4 | |
| DATE: 6/24/98 | | | | | INOC: 6/22/98 | | | | | |
| DRUG: TBT | | | | | VIRUS: HSV-2 | | | | | |
| | | | | | Specimen #3 TBT-IC50 = 2.0 μg/ml | | | | | |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 μg/ml Taxus Brevifolia Tincture (TBT) has been added.

FIGURE 8

HSV-2 ELISA, CLINICAL SPECIMEN # 4

| CC | VC | 4 | 3 | 2 | 1 | 0.75 | 0.5 | 0.25 | 0.1 | µg/ml |
|---|---|---|---|---|---|---|---|---|---|---|
| 0.012 | 0.190 | 0.026 | 0.021 | 0.059 | 0.089 | 0.018 | 0.066 | 0.115 | 0.148 | |
| 0.004 | 0.152 | 0.018 | 0.028 | 0.037 | 0.059 | 0.072 | 0.083 | 0.106 | 0.165 | |
| 0.030 | 0.199 | 0.001 | 0.042 | 0.033 | 0.026 | 0.052 | 0.065 | 0.073 | 0.195 | |
| 0.012 | 0.174 | 0.016 | 0.042 | 0.046 | 0.095 | 0.028 | 0.064 | 0.123 | 0.161 | |
| 0.020 | 0.224 | 0.033 | 0.048 | 0.027 | 0.031 | 0.025 | 0.100 | 0.078 | 0.229 | |
| 0.010 | 0.213 | 0.021 | 0.025 | 0.029 | 0.056 | 0.046 | 0.086 | 0.088 | 0.152 | |
| | | | | | | | | | | |
| 0.015 | 0.192 | 0.019 | 0.034 | 0.039 | 0.059 | 0.040 | 0.077 | 0.097 | 0.175 | |
| | | | | | | | | | | |
| | 0.177 | 0.005 | 0.020 | 0.024 | 0.045 | 0.026 | 0.063 | 0.083 | 0.160 | |
| | | | | | | | | | | |
| | | 2.5 | 11.1 | 13.4 | 25.2 | 14.4 | 35.3 | 46.5 | 90.4 | |

| DATE: 6/24/98 | INOC: 6/22/98 |
|---|---|
| DRUG: TBT | VIRUS: HSV-2 |
| | Specimen #4  TBT-IC50 = 0.25 µg/ml |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 µg/ml Taxus Brevifolia Tincture (TBT) has been added.

FIGURE 9
HSV-2 ELISA, CLINICAL SPECIMEN #5

| CC | VC | 4 | 3 | 2 | 1 | 0.75 | 0.5 | 0.25 | 0.1 | µg/ml |
|---|---|---|---|---|---|---|---|---|---|---|
| 0.016 | 0.220 | 0.041 | 0.026 | 0.052 | 0.121 | 0.134 | 0.109 | 0.159 | 0.104 | |
| 0.013 | 0.219 | 0.017 | 0.045 | 0.048 | 0.084 | 0.078 | 0.084 | 0.130 | 0.114 | |
| 0.003 | 0.128 | 0.031 | 0.067 | 0.029 | 0.069 | 0.071 | 0.043 | 0.107 | 0.120 | |
| 0.033 | 0.210 | 0.010 | 0.051 | 0.077 | 0.061 | 0.062 | 0.055 | 0.184 | 0.100 | |
| 0.022 | 0.256 | 0.025 | 0.068 | 0.094 | 0.062 | 0.083 | 0.104 | 0.131 | 0.200 | |
| 0.036 | 0.167 | 0.018 | 0.083 | 0.137 | 0.131 | 0.111 | 0.107 | 0.134 | 0.141 | |
| | | | | | | | | | | |
| 0.021 | 0.200 | 0.024 | 0.057 | 0.073 | 0.088 | 0.090 | 0.084 | 0.141 | 0.130 | |
| | | | | | | | | | | |
| | 0.180 | 0.003 | 0.036 | 0.052 | 0.068 | 0.069 | 0.063 | 0.120 | 0.109 | |
| | | | | | | | | | | |
| | | 1.8 | 20.1 | 29.2 | 37.6 | 38.6 | 35.2 | 67.0 | 60.9 | |

| DATE: 6/24/98 | INOC: 6/22/98 |
|---|---|
| DRUG: TBT | VIRUS: HSV-2 |
| | Specimen #5  TBT-IC50 = 0.5 µg/ml |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 µg/ml Taxus Brevifolia Tincture (TBT) has been added.

FIGURE 10
HSV-2 ELISA, CLINICAL SPECIMEN # 6

| CC | VC | 4 | 3 | 2 | 1 | 0.75 | 0.5 | 0.25 | 0.1 | µg/ml |
|---|---|---|---|---|---|---|---|---|---|---|
| 0.013 | 0.125 | 0.024 | 0.022 | 0.015 | 0.014 | 0.045 | 0.018 | 0.013 | 0.039 | |
| 0.012 | 0.154 | 0.028 | 0.017 | 0.111 | 0.011 | 0.077 | 0.037 | 0.055 | 0.050 | |
| 0.019 | 0.146 | 0.015 | 0.061 | 0.061 | 0.019 | 0.009 | 0.009 | 0.079 | 0.103 | |
| 0.017 | 0.128 | 0.043 | 0.021 | 0.024 | 0.124 | 0.012 | 0.037 | 0.058 | 0.075 | |
| 0.017 | 0.128 | 0.045 | 0.024 | 0.023 | 0.102 | 0.032 | 0.058 | 0.061 | 0.049 | |
| 0.033 | 0.092 | 0.029 | 0.017 | 0.033 | 0.035 | 0.061 | 0.021 | 0.082 | 0.077 | |
| | | | | | | | | | | |
| 0.019 | 0.129 | 0.031 | 0.027 | 0.045 | 0.051 | 0.039 | 0.030 | 0.058 | 0.066 | |
| | | | | | | | | | | |
| | 0.110 | 0.012 | 0.009 | 0.026 | 0.032 | 0.021 | 0.012 | 0.040 | 0.047 | |
| | | | | | | | | | | |
| | | 11.0 | 7.7 | 23.6 | 29.3 | 18.9 | 10.4 | 35.8 | 42.6 | |
| DATE: 6/24/98 | | | | | INOC: 6/22/98 | | | | | |
| DRUG: TBT | | | | | VIRUS: HSV-2 | | | | | |
| | | | | | Specimen #6 TBT-IC50 = 0.1 µg/ml | | | | | |

Column headings for the ELISA are culture control (CC) representing uninfected cell culture; Viral Control (VC), representing infected cell culture; 4-3-2-1-0.75-0.5-0.25-0.1 are viral infected cell cultures to which 4 to 0.1 µg/ml Taxus Brevifolia Tincture (TBT) has been added.

METHOD OF TREATING VIRAL INFECTIONS AND LESIONS WITH TAXANE COMPOUNDS

PRIORITY CLAIM

This application claims benefit under 35 U.S.C. §119(e) of prior Provisional Patent Application Ser. No. 60/120,582, filed Feb. 18, 1999.

FIELD OF THE INVENTION

This invention relates to compositions containing naturally occurring or synthetic taxanes or taxoids. Compositions of the present invention can be used to treat epidermal lesions, such as those resulting from viral or microbial infections.

BACKGROUND OF THE INVENTION

The herpes simplex viruses, including HSV-1 (oro-facial) and HSV-2 (genital herpes), present a serious problem for millions of people worldwide. To the best of applicant's knowledge, until now, an effective, economical, and readily available topical treatment has not existed.

Herpes simplex virus is a common, recurrent, and chronic infection. It is estimated that at least 75% of the world's population has been infected with HSV-1 and more than 20% with HSV-2. Although the majority of cases are asymptomatic, chronic outbreaks of lesions are very common, usually occurring in mucous membrane areas and the surrounding skin. The most common of these lesions occur on the lips or face and are commonly referred to as "cold sores" or "fever blisters". Genital herpes lesions occur on the genitals and buttocks and are particularly troubling because of their possible role in contributing to the spread of HIV.

Herpes lesions first appear as an area of irritation (an itching or burning sensation) known as the prodromal stage. Within a few hours, these lesions develop into small vesicles or blisters. Typically, these vesicles soon rupture and form shallow ulcerations which may scab over and heal in about ten to twenty days. The ruptured vesicles may also cause secondary infections and spread the virus to the surrounding tissue.

After initial exposure to the herpes simplex virus, the host develops antibodies that can maintain the virus in a latent state. Despite the presence of antibodies, the latent virus may be reactivated by stress, exposure to sunlight, fever, hormonal changes, menstruation, and trauma. Eruptions can occur randomly and may persist for weeks.

Paclitaxel, perhaps the most familiar of the taxanes, was first isolated in 1971 from the bark of *Taxus brevifolia*, commonly known as the Pacific Yew, and was approved in 1992 by the US Food and Drug Administration for treatment of metastatic ovarian cancer and later for breast cancer. Its mechanism of action is believed to involve promoting formation and hyperstabilization of microtubules, thereby preventing the disassembly of microtubules necessary for completion of cell division. It also has been reported that paclitaxel induces expression of cytokines, affects the activity of kinases and blocks processes essential for metastasis, in as yet uncharacterized mechanisms of action.

Paclitaxel has attracted unusually strong scientific attention, not only because of its unique antiproliferative mechanism of action, but also because it is active against nearly all cancers against which it has been tested, and because it has been discovered to be an analog of numerous, closely-related compounds occurring naturally. Taxanes are now recognized as a new class of anticancer compounds.

Research supported in part by the National Institute of Allergy and Infectious Diseases (NIAID), and conducted by virologists at the University of Chicago and the University of Alabama, has demonstrated that compounds extracted from the yew tree possess clinically significant anti-viral properties that specifically inhibit replication of HSV-1 and HSV-2 in vitro.

There is currently no known cure for herpes simplex virus infections. However, a topical therapy that delivers clinically-demonstrated, anti-viral compositions to the affected area, inhibiting viral replication in the lesions, accelerating healing of the existing lesion, and preventing the spread of secondary infections, would be of enormous benefit to the herpes sufferer.

SUMMARY OF THE INVENTION

The present invention provides compositions and methods for treating diseased, biological tissue, such as the epidermis, in a mammal. Compositions of the present invention can be used to treat epidermal lesions, such as those resulting from viral infections including, but not limited to: herpes viruses, varicella zoster virus (VZV), cytomegalovirus (CMV), Epstein-Barr virus (EBV), and papillomavirus. Compositions of the present invention can also be used to treat epidermal lesions, ulcerations, abrasions, inflammation and other conditions resulting from microbial infections. In particular, compositions of the present invention are especially adapted to treat lesions caused by herpes viruses.

In one embodiment, the present invention provides compositions useful for treating diseased, biological tissue, such as the epidermis, in a mammal. The compositions of the present invention are effective in treating viral infections, bacterial infections and inflammation. The compositions of the present invention include at least one taxane. The taxane can be a semi-synthetic taxane, such as the commercially-available taxane preparation marketed under the trademark Taxol®, or can be an entirely synthetic taxane that is chemically synthesized by any means known to those skilled in the art. Additionally, the taxane can be derived from a natural source, such as from the needles and branches of any member of the yew family (Taxaceae), such as the Pacific Yew tree (*Taxus brevifolia*), *T. baccata, T. wallichiana, T. cuspiduta, T. canadensis, T. floridana,* and others, as well as from the fungal endophyte *Taxomyces andreanae*. Preferably, compositions of the present invention include at least one taxane in an amount of from about 0.005% to about 10% of the total weight of the composition. Preferably, the compositions of the present invention also include a natural oil such as, but not limited to, olive oil, mineral oil, corn oil, sunflower oil, peanut oil, and fish oil. Preferably, the compositions of the present invention also contain a wax such as, but not limited to, beeswax, U.S.P. Carbowax 5000®, U.S.P. Carbowax 600® (the foregoing Carbowax® products are manufactured by Union Carbide Corporation, World Headquarters, 39 Old Ridgebury Road, Danbury, Conn. 06817-001) and petrolatum.

A presently preferred composition of the present invention is formed from an extract from the Pacific Yew tree (*Taxus brevifolia*) combined with virgin olive oil and beeswax. The *T. brevifolia* extract is prepared as described in Example 1 herein and combined with olive oil at a ratio of about 1:1 and the ethanol (utilized in the extraction of the *T. brevifolia* tissue) and water (from the extract) are completely evaporated before the combination of *T. brevifolia* extract and olive oil is further combined with the beeswax at a ratio of about 6:1. Preferably, the compositions of the present invention are topically applied in the form of an ointment or salve to the site of disease.

In addition to the foregoing components, compositions of the present invention can include additional ingredients including, but not limited to, analgesics and anesthetics.

In another embodiment, the present invention includes a method of treating diseased biological tissue, such as the epidermis, in a mammal. The method of the present invention includes the step of contacting a diseased biological tissue, such as the epidermis, with a composition of the present invention containing an amount of a taxane, taxoid, or related compound, that is effective to ameliorate the disease symptoms. The methods and compositions of the present invention are effective in treating viral infections, bacterial infections and inflammation. Examples of viral infections that can be treated using the compositions and method of the present invention include, but are not limited to, herpes viruses, varicella zoster virus (VZV), cytomegalovirus (CMV), Epstein-Barr virus (EBV), and papillomavirus.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1A is a Drug Screening Report for TBT which lists the analytical results for bioactive effectiveness of TBT in terms of CPE, $EC_{50}$, $CC_{50}$, $IC_{50}$, $SI=CC_{50}/EC_{50}$; Cytopathic Effect Inhibition and Plaque Reduction Assays For HSV-1, HSV-2, HCMV, MCMV, and VSV, in HFF cell cultures are detailed.

FIG. 1B is a Drug Screening Report for TBT which lists the analytical results for bioactive effectiveness of TBT in terms of CPE, $EC_{50}$, $CC_{50}$, $IC_{50}$, $SI=CC_{50}/EC_{50}$; Cytopathic Effect Inhibition and Plaque Reduction Assays For EBV in DAUDI cell cultures are detailed; Toxicity Assays in HFF and DAUDI cell cultures are detailed.

FIG. 2 is a descriptive listing of the HSV ELISA Method procedural steps used in measuring the anti-viral effectiveness of TBT to various HSV-1 and HSV-2 strains;

FIG. 3 represents the analytical $IC_{50}$ results for HSV-1 viral antigens, specifically, for HSV-1 control (ATCC #VR-733, Strain F), which demonstrated a TBT-$IC_{50}$=3 µg/ml;

FIG. 4 represents the analytical $IC_{50}$ results for HSV-1 viral antigens, specifically, for HSV-1, clinical specimen #1 (TBT-$IC_{50}$=3 µg/ml);

FIG. 5 represents the analytical $IC_{50}$ results for HSV-1 viral antigens, specifically, for HSV-1, clinical specimen #2 (TBT-$IC_{50}$=0.25 µg/ml);

FIG. 6 represents the analytical $IC_{50}$ results for HSV-2 viral antigens, specifically for HSV-2 control (ATTC #VR-734, Strain G), which demonstrated a TBT-$IC_{50}$=0.75 µg/ml;

FIG. 7 represents the analytical $IC_{50}$ results for HSV-2 viral antigens, specifically for HSV-2, clinical specimen #3 (TBT-$IC_{50}$=2.0 µg/ml);

FIG. 8 represents the analytical $IC_{50}$ results for HSV-2 viral antigens, specifically for HSV-2, clinical specimen #4 (TBT-IC50=0.25 µg/ml);

FIG. 9 represents the analytical $IC_{50}$ results for HSV-2 viral antigens, specifically for clinical specimen #5 (TBT-$IC_{50}$=0.5 µg/ml); and FIG. 10 represents the analytical $IC_{50}$ results for HSV-2 viral antigens, specifically for clinical specimen #6 (TBT-IC50<0.10 µg/ml).

DETAILED DESCRIPTION OF THE PREFERRED EMBODIMENT

In one embodiment, the present invention provides compositions useful for treating diseased, biological tissue, such as the epidermis or mucous membranes, in a mammal. The compositions of the present invention are effective in treating viral infections, bacterial infections and inflammation. The compositions of the present invention include at least one taxane. The taxane can be a semi-synthesized taxane, such as Taxol® or Taxotere®, or can be an entirely synthetic taxane that is chemically synthesized by any means known to those skilled in the art. Additionally, the taxane can be derived from a natural source, such as from the needles and branches of any member of the yew family (Taxaceae), such as the Pacific Yew tree (*Taxus brevifolia*), *T. baccata, T. wallichiana, T. cuspiduta, T. canadensis, T. floridana,* and others, as well as from the fungal endophyte *Taxomyces andreanae*. Taxanes can be extracted from a natural source by the methods set forth in Example 1 and Example 2 herein, or by any art-recognized means. Preferably, the compositions of the present invention also include a natural oil such as, but not limited to, olive oil, mineral oil, corn oil, sunflower oil, peanut oil, and fish oil. Preferably, the compositions of the present invention also contain a wax such as, but not limited to, beeswax, U.S.P. Carbowax 5000, U.S.P. Carbowax 600 and petrolatum.

A presently preferred composition of the present invention is formed from an extract from the Pacific Yew tree (*Taxus brevifolia*) combined with virgin olive oil and beeswax. The *T. brevifolia* extract is extracted by the method set forth in Example 1 herein and combined with olive oil at a ratio of about 1:1. The ethanol and water (from the extract) are completely evaporated before combining with the beeswax at a ratio of about 6:1. High Performance Liquid Chromatography (H.P.L.C.) analysis of the foregoing *T. brevifolia* extract revealed the presence of 8.1 µg/ml paclitaxel, 77.87 µg/ml cephalomannine, and 623.79 µg/ml 10-deacetyl-7-xylosyltaxol, plus some other taxanes present in minor amounts. Preferably, the compositions of the present invention are topically applied in the form of an ointment, salve or lotion to the site of disease. Compositions of the present invention can be mixed with other physiologically acceptable components, such as carriers, stabilizers or antioxidants, to form an ointment, salve or lotion having desirable physical and chemical properties, and consistency. See, Remington's Pharmaceutical Sciences, 16th Edition, Osol, A., Ed (1980).

In addition to the foregoing components, compositions of the present invention can include additional ingredients including, but not limited to, analgesics and anesthetics.

The compositions of the present invention, when applied topically, soothe the discomfort associated with viral lesions and other epidermal conditions, prevent the lesion from cracking or bleeding, reduce the time to healing, and prevent the spreading of viral infections by effectively inhibiting viral replication.

In another embodiment, the present invention includes a method of treating diseased biological tissue, such as the epidermis or mucous membranes, in a mammal. The method of the present invention includes the step of contacting a diseased biological tissue, such as the epidermis, with a composition of the present invention containing an amount of a taxane, taxoid, or related compound, that is effective to ameliorate the disease symptoms. The methods and compositions of the present invention are effective in treating viral infections, bacterial infections and inflammation. Examples of viral infections that can be treated using the compositions and method of the present invention include, but not limited to, herpes viruses, varicella zoster virus (VZV), cytomegalovirus (CMV), Epstein-Barr virus (EBV), and papillomavirus.

The compositions of the present invention should be applied directly to the affected portion of the mammalian body, such as the epidermis. Preferably, in the practice of the method of the present invention, the quantity of a composition of the present invention that is applied to an affected bodily surface is sufficient to cover the affected area. A sufficient quantity of a composition of the present invention should preferably be reapplied as often as is necessary to keep the affected area covered until the condition has completely cleared. In the case of viral infections such HSV-1 or HSV-2, a composition of the present invention should be applied at the very first (prodromal) indication of symptoms (i.e., burning, itching, or tingling sensations). Such early application will, in many cases, prevent lesions from fully developing or spreading, thus significantly limiting the time to healing, discomfort, risk of further infection to self and others, and risk of infection from other opportunistic viruses such as HIV.

The following examples merely illustrate the best mode now contemplated for practicing the invention, but should not be construed to limit the invention. Examples 1 and 2 describe methods of manufacture of various forms of the preferred embodiment. Examples 4–6 describe the clinical effectiveness of preferred embodiments applied to patients infected with HSV-1 and HSV-2. Examples 7 and 8 demonstrate the specific anti-viral activity that *Taxus brevifolia* Tinctures (TBT) exhibits in various viral infected cell culture systems.

EXAMPLE 1

Extraction of Naturally-Occurring Taxanes from Yew

Needles and branches of yew tree species are harvested by pruning the terminal branch tips of the selected species in such a way as to encourage new growth and preserve the tree for future harvesting, thus maintaining the existing biomass as a fully renewable resource. The material is then milled in order to increase the amount of exposed surfaces and render the material more compact. One part (by weight) of the material is placed in a suitable container and saturated with two parts (by weight) of ethanol (or other suitable solvent such as isopropyl alcohol, butanol, or methanol in concentrations ranging from 5% to 100%). The resulting mixture is allowed to macerate in the solvent for a specific time (typically 7 to 14 days) until the material is exhausted of its constituents, and then is hydraulically pressed and filtered to remove the residue of plant material.

EXAMPLE 2

Second Exemplary Method for Extraction of Naturally-Occurring Taxanes from Yew

The raw materials are harvested as described in Example 1 and placed in a columnar percolator. The material may be pre-moistened for several hours in a fraction of the solvent and then passed through a coarse sieve and lightly packed in the chamber, with a wad of gauze below and filter paper above. The drain is closed and sufficient solvent is added to cover the material. The vessel is then covered and allowed to macerate for approximately 24 hours. The drain is then opened and fluid is allowed through at the rate of 10 to 30 drops per minute, solvent being added to the top as needed until the material is exhausted. The material is then hydraulically pressed to extract any remaining fluid which is then added to the percolate.

EXAMPLE 3

Effectiveness of the Compositions of the Present Invention in Treating Cold Sores An adult female, suffering from severe, recurrent HSV-1 infections, applied the presently preferred composition of the invention to a labial infection (cold sore) after it had developed into a large blister (the presently preferred composition of the invention is a salve prepared from a *T. brevifolia* extract, prepared by the method set forth in Example 1 herein, which is combined with olive oil at a ratio of about 1:1. The ethanol and water (from the extract) are completely evaporated before combining *T. brevifolia* extract and olive oil with beeswax at a ratio of about 6:1.). The composition was reapplied regularly as needed to keep the blister covered. The blister disappeared within 24 hours and was replaced by healthy tissue. Several months later, the subject experienced prodromal symptoms (i.e., tingling and itching) and applied the compound immediately. Again the composition was reapplied regularly for 24 hours. The infection did not progress further and produced no lesion or other evidence of infection.

EXAMPLE 4

Effectiveness of the Compositions of the Present Invention in Treating Genital Herpes in a Female Subject An adult female, suffering from mild, recurrent HSV-2 infections that typically produced lesions on the genitalia lasting approximately 7 days, applied the presently preferred composition of the present invention to the affected parts immediately upon experiencing prodromal symptoms. The infection did not progress further and produced no lesions or other evidence of infection.

EXAMPLE 5

Effectiveness of the Compositions of the Present Invention in Treating Genital Herpes in a Male Subject An adult male, suffering from moderately severe, recurrent HSV-2 infections that typically produced lesions on the genitalia lasting approximately 7 to 10 days, applied the presently preferred composition of the invention to the affected parts immediately upon experiencing prodromal symptoms. The composition was reapplied regularly as needed to keep the affected area covered. The prodromal symptoms were resolved within 48 hours. The infection did not progress further and produced no lesions or other evidence of infection.

EXAMPLE 6

Effectiveness of the Compositions of the Present Invention in Treating Genital Herpes in a Male Subject An adult male, suffering from moderately severe, recurrent HSV-2 infections that typically produced lesions on the genitalia lasting approximately 8 days, applied the presently preferred composition of the invention to the affected parts immediately upon experiencing prodromal symptoms. Some lesions did appear and the composition was reapplied regularly as needed to keep the affected area covered. All symptoms were resolved within 4 days.

EXAMPLE 7

Screening Assays for Activity of TBT (ARB ID#980332) Against HSV-1, HSV-2, CMV, VZV, and EBV The data below, discloses the results of ELISA assays demonstrating the effectiveness of the *Taxus Brevifolia* Tinctures (TBT) extracts (Lot ARB-ID#99-332) of Example 1 against Herpes Simplex Virus-1 (HSV-1).

General Approach for Determining Antiviral Activity and Toxicity

A. Screening Assays for Activity Against HSV-1, HSV-2, CMV, and VZV

All the screening assay systems utilized have been selected to show specific inhibition of a biologic function, i.e., cytopathic effect (CPE) in susceptible human cells. In the CPE, inhibition assay, drug is added 1 hr prior to infection so the assay system will have maximum sensitivity and detect inhibitors of early replicative steps such as absorption or penetration as well as later events. To rule out non-specific inhibition of virus binding to cells all compounds that show reasonable activity in the CPE assay are conformed using a classical plaque reduction assay in which the drug is added 1 hr after infection. In the case where a compound blocks attachment, it will show up positive in the CPE assay, but may be negative by plaque assay. In this case, the plaque assay is repeated with drug being added prior to viral infection. Using this approach we have been able to identify compounds that inhibit virus absorption. These assay systems also can be manipulated by increasing the pretreatment time in order to demonstrate antiviral activity with oligodeoxynucleotides and/or peptides and by delaying addition of drug after infection, information regarding which step in the virus life cycle is inhibited (i.e., early vs. late functions) can be gained.

1. Efficacy. In all the assays used for primary screening, a minimum of six drug concentrations were used covering a range of 100 μg/ml to 0.03 μg/ml, in 5-fold increments. From these data, we calculate the dose that inhibits viral replication by 50% (effective concentration 50; $EC_{50}$) using the computer software program MacSynergy II by M. N. Prichard, K. R. Asaltine, and C. Shipman, Jr., University of Michigan, Ann Arbor, Mich.
2. Toxicity. The same drug concentrations used to determine efficacy are also used on uninfected cells in each assay to determine toxicity of each experimental compound. The drug concentration that is cytotoxic to cells as determined by their failure to take up a vital strain, neutral red, (cytotoxic concentration 50; $CC_{50}$) was determined as described above. It is very important to determine the toxicity of new compounds on dividing cells at a very early stage of testing. We have found that a cell proliferation assay using human foreskin fibroblasts (HFF) cells is a very sensitive assay for detecting drug toxicity to dividing cells and the drug concentration that inhibits cell growth by 50% ($IC_{50}$) is calculated as described above. In comparison with four human diploid cell lines and vero cells, HFF cells are the most sensitive and predictive of toxicity for bone marrow cells.
3. Assessment of Drug Activity. To determine if each compound has sufficient antiviral activity that exceeds its level of toxicity, a selectively index (SI) is calculated according to $CC_{50}/EC_{50}$. This index, also referred to as a therapeutic index was used to determine if a compound warrants further study. For these studies, a compound that had an SI of 10 or greater was evaluated in additional assay systems.

B. Confirmation of Antiviral Activity and Toxicity for HSV, CMV, and VZV

1. HSV-1 and HSV-2. Compounds that showed activity in the CPE-inhibition assay was confirmed using the plaque reduction assay as described in an earlier section. Susceptibility of additional virus strains including both lab passaged and clinical isolates was determined for selected compounds. A battery of ACV resistant HSV strains were also utilized.
2. CMV. Compounds that have activity in the CPE-inhibition assay were confirmed using the plaque reduction assay in HFF cells. A variety of laboratory, clinical, and GCV resistant isolates are also available for testing.
3. VZV. Compounds were tested for activity in a plaque reduction assay. A battery of laboratory, clinical, and ACV-resistant isolates are available.
4. Toxicity. In addition to the toxicity component incorporated into each assay system, a standardized cell cytotoxicity assay using a vital strain uptake (Neutral Red) was performed using 7 days of drug exposure to confluent non-dividing cells. This assay measures direct cell killing ($CC_{50}$). Inhibition of cell growth ($IC_{50}$) can also be determined by treatment of proliferating cells and then assessing the amount of dye uptake.

C. Assay Systems for Determining Antiviral Against EBV and Toxicity to Lymphoblast Cells 1. Superinfection of susceptible Burkitt's Lymphoma (BL) cells with P3HR-1 virus followed by analysis of specific EBV gene product expression using monoclonal antibodies provides a convenient and repeatable system of evaluate inhibition of EBV gene expression during early and late stages of the virus replication cycle. We can evaluate diffuse (D) and restricted (R) early antigens (EA) as well as viral capsid antigen (VCA) by fluorescence microscopy and by fluorescence flow cytometry.
2. Screening Assay for EBV Activity. The initial system to be used to determine antiviral activity against EBV will be VCA production Daudie cells using an immunofluorescence assay (IFA). As in all the other assays, six concentrations of drug covering a range of 100 μg/ml to 0.03 μg/ml will be utilized. Using the results obtained from untreated and drug treated cells an $EC_{50}$ can be calculated. Selected compounds that have good activity against EBV VCA production without toxicity will be tested for their ability to inhibit EBV DNA synthesis.
3. Toxicity. In each assay system utilized, drug treatment of uninfected cells is incorporated to obtain as much toxicity data as possible.
4. Confirmation of drug activity against EBV DNA production using in situ DNA hybridization assay. All compounds that have an SI>10 in the screening assay or ones selected by the project offer will be confirmed in a hybridization assay that measures the amount of EBV DNA produced by P3HR-1 infected cells. As in all other assay systems utilized, a wide range of drug concentrations will be utilized so an accurate $EC_{50}$ can be calculated. Uninfected control cells treated with drug will also be utilized as another measure of drug toxicity.
   a. Infection and drug treatment: $10^6$ cells/tube are infected with EBV at a dilution of 1:40. After incubation for 45 minutes at 37° C., 3 ml of RPMI, a cell culture media, is added and the cells pelleted by centrifugation. The supernatant was then discarded and the cells resuspended in 4 ml of RPMI needing containing various concentrations of drug. After incubation for 48 hours, the cells are counted in each tube, washed with PBS and spotted on slides. The slides are left to air-dry overnight and then fixed in acetone for 10 minutes at room temperature.

b. DNA hybridization: The biotin labeled EBV probe is added to each spot and the slide covered with a class oversleep. The slide is then heated on a hot plate at 95° C. for three minutes. After heating, the slide is left to sit at room temperature for 20 minutes, for the DNA to anneal. The oversleeps are then removed and the Post Hybridization Reagent is added to each spot. After incubation for 10 minutes and rinsing with washing buffer, Detection Reagent is applied. This is left on for 20 minutes at room temperature and then washed off with washing buffer. Chromagen Substrate Solution is added and incubated for 10 minutes at room temperature. Washing buffer is used to rinse it off, and the slides are counter stained for 30–60 seconds with fast Green stain. The slides are then rinsed with deionized water and mounted with water.

c. Reading and calculation of results: The slides are viewed in a light microscope under a magnification of 100–400. Positive cells appear as pink or red spots. All the cells are counted in several fields. The fraction of red spots in the total number of cells counted multiplied by 100 reflects the percent of hybridization.

EXAMPLE 8

ELISA Testing of HSV Susceptibility to TBT

The data below, discloses the results of ELISA assays demonstrating the effectiveness of the *T. brevifolia* tincture extracts of Example 1 against Herpes Simplex Virus (HSV).

Susceptibility Testing by ELISA (Enzyme Linked Immunosorbent Assay)

HFF cells were inoculated into 96-well microtiter trays at a density of $7 \times 10^3$ cells per well. The plates were incubated at 37° C. in 5% $CO_2$ until the cells were confluent, usually three days. Sixty wells of each plate were used: six uninfected cell control wells, six virus-infected control wells without drug, and six replicates of eight dilutions of the drug. Dilutions of each virus were prepared in minimal essential media (MEM). The growth medium was removed from all wells and 50 µl of MEM was added to the cell control wells and 50 µl of virus inoculum with a multiplicity-of-infection (MOI)~0.05, was added to the remaining wells. The virus was allowed to absorb for one hour at 37° C. The inoculum was removed and 100 µl of MEM was added to the cell control wells and the virus control wells. Eight dilutions of *Taxus brevifolia* Tincture (TBT) were prepared in MEM and 100 µl of the diluted drug was added to the remaining wells beginning at a 4.0 µg/ml through a 0.1 µg/ml of the drug. All plates were incubated at 37° C. in 5% $CO_2$.

After incubating for 48 hours, the plates were examined using an inverted phase contrast microscope to insure that viral CPE was present in the virus control wells and to score the CPE in all wells of the plate including the virus control wells and all drug dilution wells. Each row of wells was scored from 0 to 4+ and 4+ indicated that all cells showed CPE. This was done to insure that the inhibition of CPE correlated with the quantitative ELISA results. The medium was then removed from all microtiter wells and 100 µl of a blocking solution consisting of 0.5% bovine serum albumin (BSA) in phosphate buffered saline, pH 7.2, was added to each well for 30 min. at room temperature. The blocking solution was removed, the cells were fixed by adding 100 µl of ethanol/acetone (95:5, v/v) to each well and the plates were placed at −20° C. for 30 min. Each well was washed four times with 200 µl of wash solution (PBS containing 0.5% BSA and 0.05% Tween 20).

The antibodies used in ELISA were obtained from Dako Corporation, Carpinteria, Calif. and were prepared by immunizing rabbits with an antigen prepared by sonication and extraction of HSV-1 or HSV-2 infected rabbit cornea cells. All the virion proteins were present in the antigen preparation used to produce the antibody. To determine the inhibitory concentration ($IC_{50}$), the rabbit polyclonal antibody to HSV-1 or HSV-2 conjugated to horseradish peroxidase was diluted in PBS containing 10% normal rabbit serum. A volume of 100 µl of the antibody was added to each well and the plates were incubated at 37° C. for two hours. The antibody was removed and the wells were washed four times as before. The enzyme substrate, 3, 3', 5, 5'-tetramethylbenzidine (TMB, Sigma, ST. Louis, Mo.) was added to each well and the plates were incubated at room temperature for 3–4 minutes. The O.D. was determined for the uninfected cell control wells, the virus control wells, and each drug dilution. The percent change in O.D. was calculated as follows: (average drug sample O.D.—average cell control O.D.)/(average virus control O.D.—average cell control O.D.)×100. The $IC_{50}$ is defined as the dilution of antiviral compound that produces a 50% or greater reduction in the O.D. of the colored substrate product.

While the preferred embodiment of the invention has been illustrated and described, it will be appreciated that various changes can be made therein without departing from the spirit and scope of the invention.

What is claimed is:

1. A topical method of treating lesions caused by Herpes Simplex Virus 1 (HSV-1), including mucous membrane infection and inflammation, whereby said topical method comprises contacting said lesions with a composition comprising effective amounts of taxane, olive oil, and beeswax.

2. The topical method of claim 1 for treating lesions caused by HSV-1, further comprising:
   (a) rubbing said lesions with said composition; and
   (b) re-contacting and re-rubbing said lesions with said composition until lesions are resolved.

3. A topical method of treating lesions caused by Herpes Simplex Virus 1 (HSV-1), including mucous membrane infection and inflammation, whereby said topical method comprises contacting said lesions with a composition consisting essentially of effective amounts of taxane, olive oil, and beeswax.

4. The topical method of claim 3 for treating lesions caused by HSV-1, further comprising:
   (a) rubbing said lesions with said composition; and
   (b) re-contacting and re-rubbing said lesions with said composition until lesions are resolved.

5. A topical method of treating lesions caused by Herpes Simplex Virus 2 (HSV-2), including mucous membrane infection and inflammation, whereby said topical method comprises contacting said lesions with a composition comprising effective amounts of taxane, olive oil, and beeswax.

6. The topical method of claim 5 for treating lesions caused by HSV-2, further comprising:
   (a) rubbing said lesions with said composition; and
   (b) re-contacting and re-rubbing said lesions with said composition until lesions are resolved.

7. A topical method of treating lesions caused by Herpes Simplex Virus 2 (HSV-2), including mucous membrane infection and inflammation, whereby said topical method comprises contacting said lesions with a composition consisting essentially of effective amounts of taxane, olive oil, and beeswax.

8. The topical method of claim 7 for treating lesions caused by HSV-2, further comprising:
   (a) rubbing said lesions with said composition; and
   (b) re-contacting and re-rubbing said lesions with said composition until lesions are resolved.

* * * * *